United States Patent
Komata et al.

(10) Patent No.: US 7,205,443 B2
(45) Date of Patent: Apr. 17, 2007

(54) PROCESSES FOR PRODUCING FLUORINE-CONTAINING 2,4-DIOLS AND THEIR DERIVATIVES

(75) Inventors: Takeo Komata, Saitama (JP); Kei Matsunaga, Saitama (JP); Yoshiki Hirotsu, Saitama (JP); Shinya Akiba, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 246 days.

(21) Appl. No.: 11/041,940

(22) Filed: Jan. 26, 2005

(65) Prior Publication Data
US 2005/0215836 A1 Sep. 29, 2005

(30) Foreign Application Priority Data
Jan. 27, 2004 (JP) ............................. 2004-018768

(51) Int. Cl.
C07C 31/20 (2006.01)
C07C 31/18 (2006.01)
C07C 31/27 (2006.01)
C07C 67/08 (2006.01)
C07C 67/12 (2006.01)
C07C 67/14 (2006.01)

(52) U.S. Cl. ...................... 568/842; 568/841; 560/205; 560/206; 560/207; 560/210; 560/223

(58) Field of Classification Search ................ 568/842, 568/841; 560/205, 206, 207, 210, 223
See application file for complete search history.

(56) References Cited

U.S. PATENT DOCUMENTS 3,662,071 A 5/1972 Langkammerer 6,784,312 B2 8/2004 Miyazawa et al.

FOREIGN PATENT DOCUMENTS

JP 2003-40840 2/2003

Primary Examiner—Elvis O. Price
(74) Attorney, Agent, or Firm—Crowell & Moring LLP

(57) ABSTRACT

A process for producing a fluorine-containing 2,4-diol represented by the formula [4],

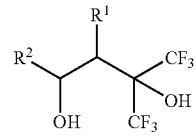

[4]

wherein $R^1$ represents a hydrogen atom or an acyclic or cyclic alkyl group having a carbon atom number of 1 to 7; $R^2$ represents an acyclic or cyclic alkyl group having a carbon atom number of 1 to 7; and $R^1$ and $R^2$ are optionally bonded to each other to form a ring, includes reducing a hydroxy ketone represented by the formula [3],

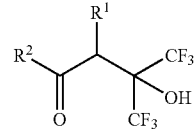

[3]

wherein $R^1$ and $R^2$ are defined as above, by hydrogen in the presence of a ruthenium catalyst.

20 Claims, No Drawings

PROCESSES FOR PRODUCING FLUORINE-CONTAINING 2,4-DIOLS AND THEIR DERIVATIVES

BACKGROUND OF THE INVENTION

The present invention relates to a process for producing fluorine-containing 2,4-diols, which are compounds useful as raw materials for monomers adapted to the next generation photoresists.

It is known that such fluorine-containing 2,4-diols have bright prospects as intermediate raw materials for monomers of the next generation resist materials and that such resists containing esters, which are formed by the bonding of the fluorine-containing 2,4-diols and acrylic acid derivatives (including acrylic acid and methacrylic acid), as their constituent element are superior in light transmission and surface adhesion (see U.S. Pat. No. 6,784,312 corresponding to Japanese Patent Laid-open Publication 2003-040840).

U.S. Pat. No. 3,662,071 discloses a process for synthesizing α-[(2-hydroxy-1-methyl-3,3,3-trifluoro-2-trifluoromethyl)propyl]benzyl alcohol by the steps of (a) heating hexafluoroacetone and propiophenone at 160° C.; and (b) reducing the product of the step (a) by aluminum isopropoxide using isopropanol as a solvent.

SUMMARY OF THE INVENTION

It is an object of the present invention to provide a process for producing a fluorine-containing 2,4-diol, which is suitable for an industrial scale production thereof.

According to the present invention, there is provided a first process for producing a fluorine-containing 2,4-diol represented by the formula [4],

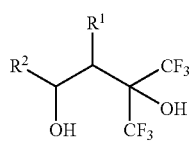

[4]

wherein $R^1$ represents a hydrogen atom or an acyclic or cyclic alkyl group having a carbon atom number of 1 to 7,
$R^2$ represents an acyclic or cyclic alkyl group having a carbon atom number of 1 to 7, and
$R^1$ and $R^2$ are optionally bonded to each other to form a ring. The first process comprises reducing a hydroxy ketone represented by the formula [3],

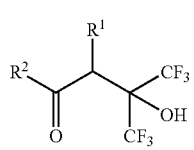

[3]

wherein $R^1$ and $R^2$ are defined as above, by hydrogen in the presence of a ruthenium catalyst.

DETAILED DESCRIPTION

It is possible by the process of U.S. Pat. No. 3,662,071 to easily produce compounds including the fluorine-containing 2,4-diol represented by the formula [4], on the laboratory level. In the step (a) of this process, hexafluoroacetone and a ketone are heated at 160° C. without using catalyst. This causes a high pressure of about 4 MPa and therefore requires the use of a reaction apparatus proof against such high pressure. It was found that, when this reaction is conducted under a pressure of 2 MPa or lower, the reaction temperature is lowered to about 100° C., thereby lowering the degree of the reaction progress to about ⅕ of that of the reaction of the after-mentioned second process of the present invention conducted in the presence of the after-mentioned additive, even if the reaction is conducted for 40 hr. In the step (b), the product of the step (a) is reduced by aluminum isopropoxide using isopropanol as a solvent. This causes a problem of the generation of wastes (e.g., aluminum wastes and an organic waste water) in large amounts. Thus, the process of U.S. Pat. No. 3,662,071 is cumbersome to be conducted in an industrial scale production.

In view of the above-mentioned problem of the prior art technique, the present inventors have eagerly studied the process for producing a fluorine-containing 2,4-diol represented by the formula [4], which is suitable for an industrial scale production thereof. As a result, we have unexpectedly found that the target compound can efficiently be produced by the above first process.

The ruthenium catalyst used in the first process can be selected from (a) metallic ruthenium, (b) a solid-phase ruthenium catalyst in which ruthenium is carried on a carrier (e.g., activated carbon, alumina, silica, and clay), (c) a ruthenium salt (e.g., $RuCl_3$, $RuBr_3$, and $Ru(NO_3)_3$), (d) a ruthenium complex (e.g., $Ru(CO)_5$, $Ru(NO)_5$, $K_4[Ru(CN)_6]$, and $Ru(phen)_3Cl_3$ where phen represents a phenanthroline), and (e) ruthenium oxide.

The reaction of the first process does not proceed well, in case that a metal other than ruthenium is used. For example, the reaction does virtually not proceed in case that a palladium-carbon catalyst is used (see the after-mentioned Comparative Example 2). As another example, in case that 1,1,1-trifluoro-2-hydroxy-2-(trifluoromethyl)pentan-4-one is brought into contact with hydrogen ($H_2$) in the presence of a platinum-carbon catalyst, the reduction into the target 1,1,1-trifluoro-2-(trifluoromethyl)pentane-2,4-diol proceeds by only 3.0% (see the after-mentioned Comparative Example 3). In contrast, it was found that the target reaction proceeds almost quantitatively under a mild condition by using a ruthenium catalyst (see the after-mentioned Examples 13 to 16).

Furthermore, we have found that the raw material in the first process, the fluorine-containing hydroxy ketone represented by the formula [3], can be produced under a mild condition by a second process according to the present invention. The second process comprises reacting hexafluoroacetone represented by the formula [1],

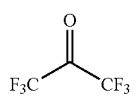

[1]

with a carbonyl compound represented by the formula [2],

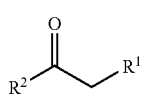
[2]

wherein R¹ and R² are defined as in the formula [4], in the presence of an additive, that is, at least one compound selected from the group consisting of fluorine-containing alcohols (e.g., 1,1,1,3,3,3-hexafluoro-2-propanol), carboxylic acids (e.g., acetic acid, propionic acid, and trifluoroacetic acid), sulfonic acids (e.g., methanesulfonic acid, paratoluenesulfonic acid, and trifluoromethanesulfonic acid), metal chlorides (e.g., aluminum chloride, tin chloride, iron chloride, and titanium chloride), inorganic acids (e.g., sulfuric acid), and $BF_3$ ($BF_3$ etherate is included as $BF_3$ in the present application). Of these, sulfuric acid is particularly preferable, since it is low in price and has a superior catalytic effect as the additive.

In the second process, the reaction is conducted in the presence of the above special additive. Due to this, the target reaction was found to proceed at a substantially low temperature. Therefore, it is possible to greatly reduce the reaction pressure.

By conducting the second process (hereinafter it may be referred to as "the first step") and the first process (hereinafter it may be referred to as "the second step") in sequence, it becomes possible to produce the target compound represented by the formula [4] under a much milder condition than that of the process of U.S. Pat. No. 3,662,071, with high yield and less amounts of wastes, by using the compound represented by the formula [1] and the compound represented by the formula [2] as the starting materials.

It is possible by a third process according to the present invention to easily produce a compound useful as a resist monomer, that is, a fluorine-containing ester compound represented by the formula [6],

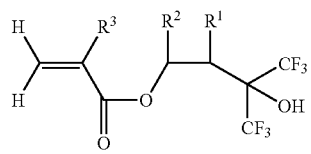
[6]

wherein R¹ and R² are defined as in the formula [4], and R³ represents H, $C_mH_{m+1}$, or $C_nF_{2n+1}$ where each of m and n represents independently an integer of 1 to 4.

The third process (hereinafter it may be referred to as "the third step") comprises reacting the fluorine-containing 2,4-diol represented by the formula [4], which is the product of the first process, with an acrylic acid derivative represented by the formula [5],

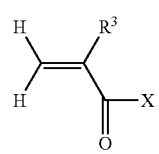
[5]

wherein R³ is defined as in the formula [6], and X represents F, Cl, or a group represented by the formula [5a],

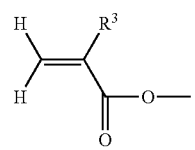
[5a]

wherein R³ is defined as in the formula [6].

The reaction scheme for conducting the second process (the first step), the first process (the second step), and the third process (the third step) in sequence can be summarized, as follows.

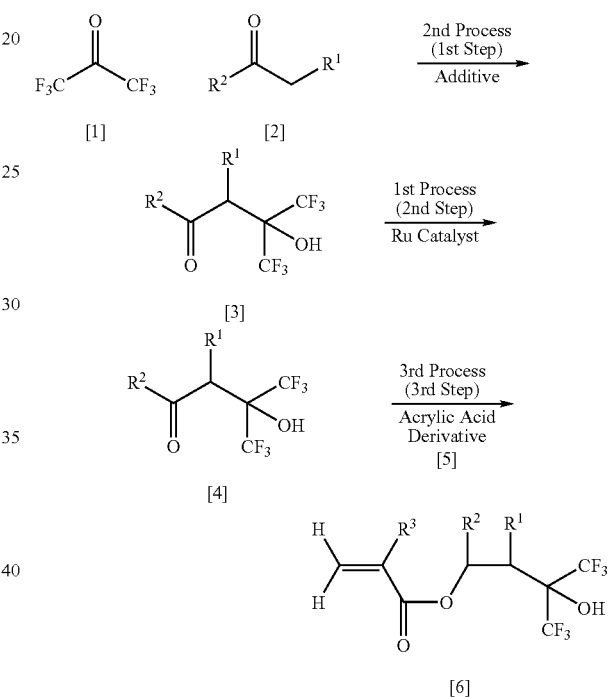

According to the present invention, it is possible to conduct the first process (the second step) alone to produce the target fluorine-containing 2,4-diol. Furthermore, as mentioned above, it is possible to produce the target fluorine-containing 2,4-diol by a combination of the first and second steps from the starting materials of 1,1,1,3,3,3-hexafluoroacetone and the carbonyl compound. This combination is a superior process for producing the fluorine-containing 2,4-diol in an industrial scale. Furthermore, the reaction of the obtained fluorine-containing 2,4-diol with the acrylic acid derivative can easily produce the fluorine-containing acrylic ester. In other words, the second and third steps can be conducted in sequence to produce the fluorine-containing acrylic ester. Furthermore, the first, second and third steps can also be conducted in sequence, as shown in the above reaction scheme.

In the invention, R¹, which can be a substituent of the carbonyl compound represented by the formula [2], represents a hydrogen atom or an acyclic or cyclic alkyl group having a carbon atom number of 1 to 7 (e.g., methyl group, ethyl group, propyl group, butyl group, pentyl group, hexyl group, heptyl group, and cyclohexyl group). $R^2$, which can be another substituent of the carbonyl compound, represents an acyclic or cyclic alkyl group having a carbon atom number of 1 to 7. Examples of the carbonyl compound (ketone) of the formula [2] include acetone, methyl ethyl ketone, methyl n-propyl ketone, isopropyl methyl ketone, methyl n-butyl ketone, methyl isobutyl ketone, pinacolone, diethyl ketone, di-n-propyl ketone, and diisopropyl ketone. Examples of the carbonyl compound (ketone), in which $R^1$ and $R^2$ are bonded to each other to form a ring, include cyclopentanone, cyclohexanone, cycloheptanone, and cyclooctanone. These ketones can be synthesized by conventional processes and are easily available as commercial reagents.

The carbonyl compound represented by the formula [2] can be acetone (i.e., $R^1$ is a hydrogen atom and $R^2$ is a methyl group in the formula [2]) as a particularly preferable example, in view of a great usefulness of the product. In case that the carbonyl compound is acetone, the product of the first step becomes 1,1,1-trifluoro-2-hydroxy-2-(trifluoromethyl)pentan-4-one represented by the formula [3a],

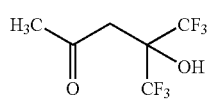

[3a]

and the product of the second step becomes 1,1,1-trifluoro-2-(trifluoromethyl)pentane-2,4-diol represented by the formula [4a].

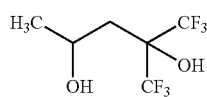

[4a]

Furthermore, preferable examples of the carbonyl compound include methyl ethyl ketone, acetophenone, cyclopentanone, cyclohexanone, and indanone.

It is possible to conduct each of the first to third steps by using a batch-wise reaction apparatus. The reaction conditions are exemplarily described in detail in the following. Certain modifications of the reaction conditions can be made by a person skilled in the art in respective reaction apparatuses.

The first step for obtaining the fluorine-containing hydroxy ketone represented by the formula [3] is described in detail, as follows.

The amount of the additive used in the first step may be from 0.0001 to 1.0 mole, preferably from 0.0005 to 0.5 moles, more preferably from 0.001 to 0.2 moles, per mol of the hexafluoroacetone. If it is less than 0.0001 moles per that, conversion of the reaction may become too low. With this, the effect of using the additive may become insufficient. If it exceeds 1.0 mole per that, the amount of the additive that is not involved in the reaction may become too much. This is economically not preferable.

In a first case that a fluorinated alcohol (e.g., 1,1,1,3,3,3-hexafluoro-2-propanol) is used as the additive, the reaction temperature of the first step may be 60 to 140° C., preferably 70 to 120° C., more preferably 80 to 110° C. If it is lower than 60° C., the reaction rate may become too low to be of a practical process. If it is higher than 140° C., the reaction pressure may become too high. This may diminish the merit of using the additive to achieve the reaction under a mild condition.

In a second case that the additive is at least one selected from carboxylic acids (e.g., acetic acid, propionic acid, and trifluoroacetic acid), sulfonic acids (e.g., methanesulfonic acid, paratoluenesulfonic acid, and trifluoromethanesulfonic acid), metal chlorides (e.g., aluminum chloride, tin chloride, iron chloride, and titanium chloride), inorganic acids (e.g., sulfuric acid), and $BF_3$ ($BF_3$ etherate is included as $BF_3$ in the present application), the effect of accelerating the reaction rate becomes higher, as compared with the first case that a fluorinated alcohol (e.g., 1,1,1,3,3,3-hexafluoro-2-propanol) is used as the additive. Thus, in the second case, the reaction temperature may be 0 to 90° C., preferably 20 to 80° C., more preferably 40 to 70° C. If it is lower than 0° C., the reaction rate may become too low to be of a practical process. Even if the reaction temperature is higher than 90° C., the reaction rate may not increase further significantly. Thus, this may be economically not preferable from the viewpoint of energy efficiency.

The carbonyl compound used in the first step may be from 0.8 to 10.0 moles, preferably from 0.9 to 5.0 moles, more preferably from 1.0 to 2.0 moles, per mol of the hexafluoroacetone. If it is less than 0.8 moles per that, both of the reaction selectivity and the target compound yield may become too low. If it is greater than 10.0 moles per that, the amount of the carbonyl compound that is not involved in the reaction may become too much. This may increase a waste disposal load and thus may be economically not preferable.

In the first step, it is preferable to use a solvent that is capable of dissolving the carbonyl compound (ketone) in case that the carbonyl compound is in the form of solid. With this, the reaction can proceed particularly smoothly. The type of this solvent is not particularly limited. Its examples include hydrocarbons (e.g., pentane, hexane, octane, and cyclohexane) and ethers (e.g., diethyl ether, methyl-t-butyl ether, diisopropyl ether, and tetrahydrofuran). It is possible to use a single or plurality of solvents.

The reaction time to complete the first step depends on the reaction temperature and the type and the amount of the additive. It is preferable to conduct the reaction, while checking the reaction progress by a suitable means such as gas chromatography, thin-layer chromatography, etc. The inside pressure of the reactor depends on whether or not the raw material hexafluoroacetone (gas) exists in the reactor. Therefore, it is effective to determine the reaction termination by observing the pressure change.

The reactor used in each of the first step, the second step, and the after-mentioned first and second cases of the third step may be made of a resin material (e.g., ethylene tetrafluoride resin, chlorotrifluoroethylene resin, vinylidene fluoride resin, and PFA resin). It may be one lined with glass or the like. Furthermore, it may be a glass or stainless steel vessel.

The second step for obtaining the fluorine-containing 2,4-diol represented by the formula [4] is described in detail, as follows. In the second step, the raw material, the fluorine-containing hydroxy ketone represented by the formula [3], may be one obtained by the first step. This is economically preferable.

The ruthenium catalyst used in the second step is preferably a solid phase catalyst in which ruthenium is carried on a carrier (e.g., activated carbon, alumina, and silica), since such solid phase catalyst has high activity, high stability and handling easiness. The solid phase catalyst can be prepared, for example, by impregnating a carrier with a ruthenium salt solution, followed by a reduction treatment with $H_2$ gas under heating. In particular, it is possible to easily obtain Ru/C (ruthenium-carbon catalyst in which ruthenium is carried on activated carbon), ruthenium-alumina catalyst, and ruthenium-silica catalyst as commercial products. These catalysts are preferable due to their high activities. These catalysts can particularly easily be handled, if they contain a certain amount of water (e.g., 50 wt % of water base on the total weight of the catalyst). Although the catalyst is not particularly limited with respect to the ruthenium content of the catalyst solid matter (i.e., the component other than water), that of about 2–10 wt % (e.g., 5 wt %) is preferable due to its easy availability, high stability and easy handling.

The reaction of the second step can be conducted in the presence of a plurality of ruthenium catalysts. However, such reaction does not have a particular merit.

The amount of the ruthenium catalyst used in the second step may be 0.0002 to 0.04 moles, preferably 0.0004 to 0.02 moles, more preferably 0.001 to 0.01 moles, in terms of mole number of Ru atoms, per mol of the fluorine-containing hydroxy ketone. If it is less than 0.0002 moles per that, the reaction rate may become too low. The use of greater than 0.04 moles per that is economically not preferable.

In the second step, it is possible to supply hydrogen under a pressure of normal pressure (0.1 MPa) to 5 MPa. It is, however, preferable to supply hydrogen under a pressurized condition. With this, it is possible to increase the reaction rate, and the operation becomes easy. Specifically, the hydrogen pressure is preferably 0.15 to 2 MPa, more preferably 0.3 to 1 MPa. Although it is possible to conduct the reaction under a pressure lower than normal pressure, the reaction may become slow. Furthermore, the facility becomes complicated. Thus, the reaction under such low pressure does not have a particular merit.

The above-explained ruthenium catalyst is highly stable and therefore can be used in the air. It is, however, particularly effective to conduct the reaction under a condition that the atmosphere of the reactor has been replaced with hydrogen gas to remove the air (oxygen) from the reactor. With this, it is possible to maintain the ruthenium catalyst activity to a higher level.

In the second step, it is preferable to use solvent. This allows the reaction to proceed particularly smoothly. The type of the solvent usable in the second step is not particularly limited. Its examples include aromatic compounds (e.g., benzene, toluene, xylene, and mesitylene), ethers (e.g., diethyl ether, methyl-t-butyl ether, diisopropyl ether, and tetrahydrofuran), and alcohols (e.g., methanol, ethanol, propanol, 2-propanol, trifluoroethanol, and 1,1,1,3,3,3-hexafluoro-2-propanol). These solvents can be used singly or in combination.

The solvent for the second step may be in an amount of 0.005 to 100 g, preferably 0.01 to 20 g, more preferably 0.1 to 10 g, per gram of the hydroxy ketone represented by the formula [3]. Exceeding 100 g may be economically not preferable from the viewpoint of productivity.

The reaction temperature for conducting the second step may be 0 to 150° C., preferably 30 to 120° C., more preferably 50 to 90° C. If it is lower than 0° C., the reaction rate may become too low to be of a practical process. Even if the reaction temperature is higher than 150° C., the reaction rate may not increase further significantly. Thus, this may be economically not preferable from the viewpoint of energy efficiency.

The reaction time to complete the second step depends on the reaction temperature and the type and the amount of the catalyst. It is preferable to terminate the reaction at the time when the $H_2$ consumption has virtually been completed, while checking the condition of $H_2$ consumption by, for example, the inside pressure of the reactor.

The third step for synthesizing the fluorine-containing ester compound represented by the formula [6] is explained in detail, as follows.

The substituent $R^3$ of the acrylic acid derivative represented by the formula [5] is particularly preferably a hydrogen atom, methyl group or trifluoromethyl group, due to the usefulness of the target product represented by the formula [6] having such $R^3$.

The third step may be conduced by a normal esterification. Its particulars are described in detail, as follows. At first, there is described in detail a first case of the third step that the acrylic acid derivative represented by the formula [5] is an α-substituted acrylic halide (i.e., X=Cl or F in the formula [5]).

In the first case, it is preferable to conduct the third step in the presence of a base. This base is preferably at least one selected from trimethylamine, triethylamine, pyridine, 2,6-dimethylpyridine, dimethylaminopyridine, sodium carbonate, potassium carbonate, sodium hydroxide, and potassium hydroxide. Of these, pyridine and 2,6-dimethylpyridine are particularly preferable.

The above base to used in the third step may be in an amount of 0.2 to 2.0 moles, preferably 0.5 to 1.5 moles, more preferably 0.9 to 1.2 moles, per mol of the fluorine-containing 2,4-diol represented by the formula [4]. If it is less than 0.2 moles per that, selectivity of the reaction and yield of the target product may become too low. If it exceeds 2.0 moles, the amount of the base that is not involved in the reaction may become too much. Thus, this may be economically not preferable.

The α-substituted acrylic halide to be used in the third step may be in an amount of 0.2 to 2.0 moles, preferably 0.5 to 1.5 moles, more preferably 0.9 to 1.2 moles, per mol of the fluorine-containing 2,4-diol. If it is less than 0.2 moles per that, selectivity of the reaction and yield of the target product may become too low. If it exceeds 2.0 moles per that, the amount of the α-substituted acrylic halide that is not involved in the reaction may become too much. This increases a waste disposal load and thus may be economically not preferable.

In case that the acrylic acid derivative represented by the formula [5] is an α-substituted acrylic halide, a hydrofluoride or hydrochloride of the base precipitates as a by-product in the third step. In this case, it is necessary to use solvent to improve operability of the reaction. The type of this solvent is not particularly limited. Its examples include aromatic compounds (e.g., benzene, toluene, xylene, and mesitylene), ethers (e.g., diethyl ether, methyl-t-butyl ether, diisopropyl ether, and tetrahydrofuran), and halogen-containing compounds (e.g., methylene chloride, chloroform, and carbon tetrachloride). These solvents can be used singly or in combination.

The above-mentioned solvent may be in an amount of 0.5 to 100 g, preferably 1.0 to 20 g, more preferably 2.0 to 10 g, per gram of the fluorine-containing 2,4-diol. If it is less than 0.5 g per that, the slurry concentration of the hydrochloride of the base may become too high, thereby lowering the operability. Exceeding 100 g per that may be economically not preferable from the viewpoint of the productivity.

In the first case of the third step, the reaction temperature may be −50 to 200° C., preferably −20 to 150° C., more preferably 0 to 120° C. If it is lower than −50° C., the reaction rate may become too low to be of a practical production process. If it is higher than 200° C., the raw material α-substituted acrylic halide or the target fluorine-containing ester compound represented by the formula [6] may polymerize. Thus, this may be not preferable.

In the first case of the third step, it is optional to conduct the reaction in the presence of a polymerization inhibitor for the purpose of suppressing polymerization of the α-substituted acrylic halide or the fluorine-containing ester compound. The polymerization inhibitor may be at least one compound selected from 2,5-di-t-butylhydroquinone, 1,2,4-trihydroxybenzene, 2,5-bistetramethylbutylhydroquinone, leucoquinizarin, phenothiazine, tetraethylthiuram, disulfide, 1,1-diphenyl-2-picrylhydrazyl, and 1,1-diphenyl-2-picrylhydrazine. Further examples of the polymerization inhibitor expressed in trade name, together with compound name in parenthesis, include NONFLEX F (N,N'-di-2-naphthyl-p-phenylenediamine), NONFLEX H (N,N'-diphenyl-p-phenylenediamine), NONFLEX DCD (4,4'-bis(α,α'-dimethylbenzyl)diphenylamine), NONFLEX MBP (2,2'-methylene-bis(4-methyl-6-tert-butylphenol), and OZONONE 35 (N-(1-methylheptyl)-N'-phenyl-p-phenylenediamine) of SEIKO CHEMICAL Co., Ltd located in Japan, and Q-1300 (N-nitrosophenylhydroxylamine ammonium salt) and Q-1301 (N-nitrosophenylhydroxylamine alminium salt) of Wako Pure Chemical Industries, Ltd. located in Japan. All of the above examples of the polymerization inhibitor are easily available as commercial products.

In the first case of the third step, the polymerization inhibitor may be in an amount of 0 to 0.1 moles, preferably 0.00001 to 0.05 moles, more preferably 0.0001 to 0.01 moles, per mol of the fluorine-containing 2,4-diol. Even if it exceeds 0.1 moles per that, the effect of suppressing the polymerization may not improve further. Thus, this may be economically not preferable.

In the following, there is described in detail a second case of the third step that the acrylic acid derivative represented by the formula [5] is an α-substituted acrylic acid anhydride (i.e., X of the formula [5] represents a group represented by the formula [5a]).

In the second case of the third step, the α-substituted acrylic acid anhydride may be in an amount of 0.5 to 5.0 moles, preferably 0.7 to 3.0 moles, more preferably 1.0 to 2.0 moles, per mol of the fluorine-containing 2,4-diol. If it is less than 0.5 moles per that, conversion of the reaction and yield of the target product may become insufficient. If it is greater than 5.0 moles per that, the amount of the α-substituted acrylic acid anhydride that is not involved in the reaction may become too much. This may be economically not preferable due to the waste disposal load.

In the second case of the third step, it is possible to add an additive to accelerate the reaction. This additive is preferably at least one acid selected from organic sulfonic acids (e.g., methanesulfonic acid, ethanesulfonic acid, p-toluenesulfonic acid, benzenesulfonic acid, and trifluoromethanesulfonic acid) and Lewis acids. The additive may be in an amount of 0.01 to 2.0 moles, preferably 0.02 to 1.8 moles, more preferably 0.05 to 1.5 moles, per mol of the fluorine-containing 2,4-diol. If it is less than 0.01 moles per that, conversion of the reaction and yield of the target product may become too low. If it is greater than 2.0 moles per that, the amount of the additive that is not involved in the reaction may become too much. This may be economically not preferable.

In the second case of the third step, if the additive is not added, the reaction temperature may be 80 to 200° C., preferably 100 to 180° C., more preferably 120 to 160° C. If it is lower than 80° C., the reaction rate may become too low. If it is higher than 200° C., the α-substituted acrylic acid anhydride or the fluorine-containing ester compound may polymerize. In contrast, if the additive is added in the second case of the third step, it may be 0 to 80° C., preferably 10 to 70° C., more preferably 20 to 60° C. If it is lower than 0° C., the reaction rate may become too low to be of a practical production process. If it is higher than 80° C., side reactions tend to occur, thereby lowering selectivity of the target fluorine-containing ester compound. Thus, it is preferable to add the additive in the second case of the third step, since it is possible to obtain a sufficient reactivity and an improved selectivity with a relatively low temperature. For example, it is a particularly preferable embodiment in the second case of the third step that the reaction is conducted at a temperature of 20 to 60° C. in the presence of an additive that is at least one acids selected from methanesulfonic acid, ethanesulfonic acid, p-toluenesulfonic acid, benzensulfonic acid, and trifluoromethanesulfonic acid.

In the second case of the third step, the reaction can proceed without solvent. It is, however, preferable to use solvent in order to obtain homogeneity of the reaction and to improve operability after the reaction. The type of the solvent is not particularly limited. Its examples may be the same as those used in the first case of the third step. Such solvents may be used singly or in combination.

The solvent to be used in the second case of the third step may be 0.1 to 100 g, preferably 0.5 to 50 g, more preferably 1.0 to 20 g, per gram of the fluorine-containing 2,4-diol. If it is less than 0.1 g per that, the merit of using the solvent may be insufficient. Exceeding 100 g per that may be economically not preferable from the viewpoint of productivity.

In the second case of the third step, it is optional to conduct the reaction in the presence of a polymerization inhibitor for the purpose of suppressing polymerization of the α-substituted acrylic acid anhydride or the fluorine-containing ester compound. The polymerization inhibitor may be at least one compound selected from hydroquinone, methoquinone, 2,5-di-t-butylhydroquinone, 1,2,4-trihydroxybenzene, 2,5-bistetramethylbutylhydroquinone, leucoquinizarin, phenothiazine, tetraethylthiuram, disulfide, 1,1-diphenyl-2-picrylhydrazyl, and 1,1-diphenyl-2-picrylhydrazine. Further examples of the polymerization inhibitor expressed in trade name include NONFLEX F, NONFLEX H, NONFLEX DCD, NONFLEX MBP, and OZONONE 35 of SEIKO CHEMICAL Co., Ltd located in Japan, and Q-1300 and Q-1301 of Wako Pure Chemical Industries, Ltd. located in Japan.

In the second case of the third step, the polymerization inhibitor may be in an amount of 0.00001 to 0.1 moles, preferably 0.0001 to 0.05 moles, more preferably 0.001 to 0.01 moles, per mol of the fluorine-containing 2,4-diol. Even if it exceeds 0.1 moles per mol of that, the effect of suppressing the polymerization may not improve further. Thus, this may be economically not preferable.

For example, the first step for producing the hydroxy ketone represented by the formula [3] can be conducted, as follows. At first, a reactor proof against the reaction conditions of the first step is charged with the carbonyl compound and the additive, followed by closing the reactor. Then, hexafluoroacetone is gradually introduced into the reactor from a hexafluoroacetone cylinder. The reaction is conducted with cooling or heating from outside according to need. The consumption of the raw material is monitored by sampling or the like. Once the termination of the reaction has been found by monitoring the consumption of the raw material, the reaction liquid is cooled down. The resulting hydroxy ketone can be purified by a normal conventional method. For example, it is possible to easily obtain this compound by subjecting the reaction liquid to distillation.

For example, the second step for producing the fluorine-containing 2,4-diol represented by the formula [4] can be conducted, as follows. At first, a reactor proof against the reaction conditions of the second step is charged with the hydroxy ketone, which can be the product of the first step, solvent and the ruthenium catalyst, followed by tightly closing the reactor. The reaction is conducted under heating from outside, while hydrogen gas is supplied into the reactor to maintain a predetermined pressure. The consumption of the raw material is monitored by sampling or the like. Once the termination of the reaction has been found by monitoring the consumption of the raw material, the reaction liquid is cooled down. The resulting fluorine-containing 2,4-diol can be purified by a normal conventional method. For example, the catalyst is separated from the reaction liquid by filtration, and then the resulting filtrate is subjected to distillation. With this, it is possible to easily obtain the target compound.

For example, it is possible to conduct the first case of the third step that the acrylic acid derivative represented by the formula [5] is an α-substituted acrylic halide (i.e., X=Cl or F in the formula [5]), for producing the fluorine-containing ester compound represented by the formula [6], as follows. At first, a reactor proof against the reaction conditions is charged with base, solvent, the fluorine-containing 2,4-diol represented by the formula [4], the α-substituted acrylic halide and polymerization inhibitor. Then, the reaction is conducted with stirring under heating from outside. The consumption of the raw material is monitored by sampling or the like. Once the termination of the reaction has been found by monitoring the consumption of the raw material, the reaction liquid is cooled down.

The fluorine-containing ester compound obtained in the first case of the third step can be purified by a normal conventional method. For example, a hydrochloride of the base, contained in the reaction liquid, is removed by filtration. The resulting filtrate is sequentially treated with a hydrochloric acid aqueous solution, a sodium carbonate aqueous solution, and a sodium chloride aqueous solution in this order, followed by distilling the solvent out, thereby obtaining a crude organic matter. This crude organic matter can be purified, for example, by column chromatography or distillation, thereby obtaining the target product of high purity.

For example, it is possible to conduct the second case of the third step that the acrylic acid derivative represented by the formula [5] is an α-substituted acrylic acid anhydride (i.e., X of the formula [5] represents a group represented by the formula [5a]), for producing the fluorine-containing ester compound represented by the formula [6], as follows. At first, a reactor proof against the reaction conditions is charged with solvent, the fluorine-containing 2,4-diol represented by the formula [4], the α-substituted acrylic acid anhydride, polymerization inhibitor and additive. Then, the reaction is conducted with stirring under heating from outside. The consumption of the raw material is monitored by sampling or the like. Once the termination of the reaction has been found by monitoring the consumption of the raw material, the reaction liquid is cooled down.

The fluorine-containing ester compound obtained in the second case of the third step can be purified by a normal conventional method. For example, the reaction liquid is sequentially treated with water, a sodium hydrogen carbonate aqueous solution, and brine in this order, followed by distilling the solvent out, thereby obtaining a crude organic matter. This crude organic matter can be purified, for example, by column chromatography or distillation, thereby obtaining the target product of high purity.

The following nonlimitative examples are illustrative of the present invention. Herein, the percent (%) of the compositional analysis value refers to area 1% of an organic component obtained by gas chromatography of a sampled reaction mixture.

EXAMPLE 1

1st Step

Production of 1,1,1-Trifluoro-2-hydroxy-2-(trifluoromethyl)pentan-4-one

A 1000 mL pressure-proof glass reactor equipped with a stirrer, a pressure gauge, a thermometer and a gas introducing tube was charged with 133.0 g (2.29 moles) of acetone and 0.40 g of concentrated sulfuric acid, followed by introducing 190.0 g (1.14 moles) of 1,1,1,3,3,3-hexafluoroacetone with stirring at a temperature range of 50 to 60° C. by spending 2 hr. Upon this, the pressure was 0.4 MPa in absolute pressure (hereinafter all the pressure values are in absolute pressure). After introducing 1,1,1,3,3,3-hexafluoroacetone, the reaction liquid was stirred at a temperature of 50 to 60° C. for 3 hr. When the pressure lowered to 0.1 MPa, the reaction was terminated. Then, the reaction liquid was sampled, and its composition was analyzed by gas chromatography. With this, it was found to contain 86.84% of the target 1,1,1-trifluoro-2-hydroxy-2-(trifluoromethyl)pentan-4-one, 2.47% of 1,3-bis(2'-hydroxy-1',1',1',3',3',3'-hexafluoropropyl)acetone as an impurity and 10.69% of other impurities, except excessive acetone. 321.1 g of the obtained reaction mixture were subjected to a vacuum distillation under 4.8 kPa (1.0 kPa=7.5 Torr), thereby collecting a distillate having a boiling point range of 67 to 68° C. With this, 162.0 g of the target 1,1,1-trifluoro-2-hydroxy-2-(trifluoromethyl)pentan-4-one (purity: 99.5%) were obtained. The yield was 63.1%.

The NMR data of the target product are as follows.

$^1$H NMR (solvent: CDCl$_3$; standard substance: TMS); δ 6.78 (s, 1H), 2.96 (s, 2H), 2.34 (s, 3H) $^{19}$F NMR (solvent: CDCl$_3$; standard substance: CCl$_3$F); δ −76.2 (s, 6F)

EXAMPLE 2

1st Step

Production of 1,1,1-Trifluoro-2-hydroxy-2-(trifluoromethyl)pentan-4-one

A 1-liter pressure-proof stainless steel (SUS316) reactor equipped with a pressure gauge, a thermometer and a stirrer was charged with 261.50 g (4.50 moles) of acetone, 5.05 g (0.030 moles) of 1,1,1,3,3,3-hexafluoro-2-propanol, and 498.0 g (3.00 moles) of 1,1,1,3,3,3-hexafluoroacetone, followed by heating in an oil bath to get an internal temperature of 100° C. Upon this, the pressure was 1.81 MPa. 1 hr later the pressure became 1.94 MPa. After that, the pressure lowered gradually. 2 hr after the internal temperature reached 100° C., the pressure became 0.29 MPa. 1 hr later (i.e., 3 hr after the internal temperature reached 100° C.), it was cooled down to room temperature to terminate the reaction. Then, the reaction liquid was sampled, and its composition was analyzed by gas chromatography. With this, it was found to contain 70.2% of the target 1,1,1- trifluoro-2-hydroxy-2-(trifluoromethyl)pentan-4-one, 25.5% of 1,3-bis(2'-hydroxy-1',1',1',3',3',3'-hexafluoropropyl)acetone as an impurity and 4.3% of other impurities, except excessive acetone and 1,1,1,3,3,3-hexafluoro-2-propanol as an additive. 764.55 g of the obtained reaction mixture were subjected to a vacuum distillation under 4.8 kPa, thereby collecting a distillate having a boiling point range of 67 to 68° C. With this, 361.87 g of the target 1,1,1-trifluoro-2-hydroxy-2-(trifluoromethyl)pentan-4-one (purity: 99.7%) were obtained. The yield was 53.7%. The NMR data of the product were the same as those of Example 1.

EXAMPLE 3

1st Step

A 100 mL pressure-proof glass reactor equipped with a pressure gauge, a thermometer and a gas introducing tube was charged with a stirring magnet covered with tetrafluoroethylene resin, 13.3 g (0.23 moles) of acetone, and 0.04 g (0.28 mmol) of $BF_3$ etherate (boron trifluoride diethyletherate, $(C_2H_5)_2O \cdot BF_3$), followed by introducing 19.0 g (0.11 moles) of 1,1,1,3,3,3-hexafluoroacetone with stirring using a stirrer at a temperature range of 50 to 60° C. by spending 1 hr. Upon this, the pressure was 0.5 MPa. After introducing 1,1,1,3,3,3-hexafluoroacetone, the reaction liquid was stirred at a temperature of 50 to 60° C. for 2 hr. When the pressure lowered to 0.1 MPa, the reaction was terminated. As a result, 32.3 g of a reaction mixture were obtained. The reaction liquid, except excessive acetone, was found by gas chromatography to contain 62.63% of the target 1,1,1-trifluoro-2-hydroxy-2-(trifluoromethyl)pentan-4-one, 24.04% of 1,3-bis(2'-hydroxy-1',1',1',3',3',3'-hexafluoropropyl)acetone as an impurity and 13.33% of other impurities.

EXAMPLE 4

1st Step

Example 3 was repeated except in that $BF_3$ etherate was replaced with 0.04 g (0.27 mmol) of trifluoromethanesulfonic acid. As a result, 32.3 g of a reaction mixture were obtained. The reaction liquid, except excessive acetone, was found by gas chromatography to contain 65.13% of the target 1,1,1-trifluoro-2-hydroxy-2-(trifluoromethyl)pentan-4-one, 1.23% of 1,3-bis(2'-hydroxy-1',1',1',3',3',3'-hexafluoropropyl)acetone as an impurity and 33.64% of other impurities.

EXAMPLE 5

1st Step

Example 3 was repeated except in that $BF_3$ etherate was replaced with 0.04 g (0.35 mmol) of trifluoroacetic acid. As a result, 32.3 g of a reaction mixture were obtained. The reaction liquid, except excessive acetone, was found by gas chromatography to contain 66.10% of the target 1,1,1-trifluoro-2-hydroxy-2-(trifluoromethyl)pentan-4-one, 31.92% of 1,3-bis(2'-hydroxy-1',1',1',3',3',3'-hexafluoropropyl)acetone as an impurity and 1.98% of other impurities.

EXAMPLE 6

1st Step

Example 3 was repeated except in that $BF_3$ etherate was replaced with 0.04 g (0.26 mmol) of titanium trichloride. As a result, 32.3 g of a reaction mixture were obtained. The reaction liquid, except excessive acetone, was found by gas chromatography to contain 77.09% of the target 1,1,1-trifluoro-2-hydroxy-2-(trifluoromethyl)pentan-4-one, 18.51% of 1,3-bis(2'-hydroxy-1',1',1',3',3',3'-hexafluoropropyl)acetone as an impurity and 4.40% of other impurities.

EXAMPLE 7

1st Step

Example 3 was repeated except in that $BF_3$ etherate was replaced with 0.04 g (0.21 mmol) of titanium tetrachloride. As a result, 32.3 g of a reaction mixture were obtained. The reaction liquid, except excessive acetone, was found by gas chromatography to contain 70.31% of the target 1,1,1-trifluoro-2-hydroxy-2-(trifluoromethyl)pentan-4-one, 19.11% of 1,3-bis(2'-hydroxy-1',1',1',3',3',3'-hexafluoropropyl)acetone as an impurity and 10.58% of other impurities.

EXAMPLE 8

1st Step

Production of 6,6,6-Trifluoro-5-hydroxy-5-(trifluoromethyl)hexan-3-one

A 1000 mL pressure-proof glass reactor equipped with a stirrer, a pressure gauge, a thermometer and a gas introducing tube was charged with 260.0 g (3.60 moles) of acetone and 0.80 g of concentrated sulfuric acid, followed by introducing 400.0 g (2.40 moles) of 1,1,1,3,3,3-hexafluoroacetone with stirring at a temperature range of 50 to 60° C. by spending 5.5 hr. Upon this, the pressure was 0.5 MPa. After introducing 1,1,1,3,3,3-hexafluoroacetone, the reaction liquid was stirred at a temperature of 50 to 60° C. for 3 hr. When the pressure lowered to 0.1 MPa, the reaction was terminated. The sampled reaction liquid, except excessive acetone, was found by gas chromatography to contain 85.00% of the target 6,6,6-trifluoro-5-hydroxy-5-(trifluoromethyl)hexan-3-one, 7.80% of 5,5,5-trifluoro-4-hydroxy-3-methyl-4-(trifluoromethyl)pentan-2-one as an impurity and 7.20% of other impurities. 687.0 g of the obtained reaction mixture were subjected to a vacuum distillation under 12 kPa, thereby collecting a distillate having a boiling point range of 99.3 to 99.6° C. With this, there were obtained 298.0 g of a mixture containing 97.00% of the target 6,6,6-trifluoro-5-hydroxy-5-(trifluoromethyl)hexan-3-one and 2.40% of 5,5,5-trifluoro-4-hydroxy-3-methyl-4-(trifluoromethyl)pentan-2-one. The yield of 6,6,6-trifluoro-5-hydroxy-5-(trifluoromethyl)hexan-3-one was 50.6%.

The NMR data of the target product are as follows.
$^1$H NMR (solvent: $CDCl_3$; standard substance: TMS); δ 6.86 (s, 1H), 2.92 (s, 2H), 2.61 (q, J=7.22 Hz, 2H), 1.11 (t, J=7.22 Hz, 3H) $^{19}$F NMR (solvent: $CDCl_3$; standard substance: $CCl_3F$); δ −78.8 (s, 6F)

EXAMPLE 9

1st Step

Production of 2-[2,2,2-trifluoro-1-hydroxy-1-(trifluoromethyl)ethyl]cyclohexanone A 100 mL pressure-proof glass reactor equipped with a pressure gauge, a thermometer and a gas introducing tube was charged with a stirring magnet coated with tetrafluoroethylene resin, 14.1 g (0.14 moles) of cyclohexanone and 0.04 g of concentrated sulfuric acid, followed by introducing 20.0 g (0.12 moles) of 1,1,1,3,3,3-hexafluoroacetone with stirring using a stirrer at a temperature range of 50 to 60° C. by spending 2 hr. Upon this, the pressure was 0.5 MPa. After introducing 1,1,1,3,3,3-hexafluoroacetone, the reaction liquid was stirred at a temperature of 50 to 60° C. for 3 hr. When the pressure lowered to 0.1 MPa, the reaction was terminated. As a result, 34.1 g of a reaction mixture were obtained. The reaction liquid, except excessive acetone, was found by gas chromatography to contain 56.2% of the target 2-[2,2,2-trifluoro-1-hydroxy-1-(trifluoromethyl)ethyl]cyclohexanone and 43.8% of impurities. 34.1 g of the obtained reaction mixture were subjected to a vacuum distillation under 2.2 kPa, thereby collecting a distillate having a boiling point range of 98 to 100° C. With this, there were obtained 15.5 g of the target 2-[2,2,2-trifluoro-1-hydroxy-1-(trifluoromethyl)ethyl]cyclohexanone (purity: 98.0%). The yield was 47.9%.

The NMR data of the target product are as follows.

$^1$H NMR (solvent: CDCl$_3$; standard substance: TMS); δ 7.25 (s, 1H), 2.99–3.04 (m, 1H), 1.64–2.58 (m, 8H) $^{19}$F NMR (solvent: CDCl$_3$; standard substance: CCl$_3$F); δ −72.6 (q, J=10.2 Hz, 3F), −76.8 (q, J=10.2 Hz, 3F).

EXAMPLE 10

1st Step

Production of 2-[2,2,2-trifluoro-1-hydroxy-1-(trifluoromethyl)ethyl]cyclopentanone A 100 mL pressure-proof glass reactor equipped with a pressure gauge, a thermometer and a gas introducing tube was charged with a stirring magnet coated with tetrafluoroethylene resin, 12.2 g (0.14 moles) of cyclopentanone and 0.04 g of concentrated sulfuric acid, followed by introducing 20.0 g (0.12 moles) of 1,1,1,3,3,3-hexafluoroacetone with stirring using a stirrer at a temperature range of 50 to 60° C. by spending 2 hr. Upon this, the pressure was 0.5 MPa. After introducing 1,1,1,3,3,3-hexafluoroacetone, the reaction liquid was stirred at a temperature of 50 to 60° C. for 3 hr. When the pressure lowered to 0.1 MPa, the reaction was terminated. As a result, 32.2 g of a reaction mixture were obtained. The reaction liquid, except excessive cyclopentanone, was found by gas chromatography to contain 86.6% of the target 2-[2,2,2-trifluoro-1-hydroxy-1-(trifluoromethyl)ethyl]cyclopentanone and 13.4% of impurities. 32.2 g of the obtained reaction mixture were subjected to a vacuum distillation under 2.9 kPa, thereby collecting a distillate having a boiling point range of 81 to 83° C. With this, there were obtained 25.0 g of the target 2-[2,2,2-trifluoro-1-hydroxy-1-(trifluoromethyl)ethyl]cyclopentanone (purity: 98.3%). The yield was 81.6%.

The NMR data of the target product are as follows.

$^1$H NMR (solvent: CDCl$_3$; standard substance: TMS); δ 7.01 (s, 1H), 2.02–2.64 (m, 6H), 1.71–1.83 (m, 1H) $^{19}$F NMR (solvent: CDCl$_3$; standard substance: CCl$_3$F); δ −72.5 (q, J=9.16 Hz, 3F), −78.3 (q, J=9.16 Hz, 3F).

EXAMPLE 11

1st Step

Production of 4,4,4-trifluoro-3-hydroxy-1-phenyl-3-(trifluoromethyl)butan-1-one

A 100 mL pressure-proof glass reactor equipped with a pressure gauge, a thermometer and a gas introducing tube was charged with a stirring magnet coated with tetrafluoroethylene resin, 17.3 g (0.14 moles) of acetophenone and 0.04 g of concentrated sulfuric acid, followed by introducing 20.0 g (0.12 moles) of 1,1,1,3,3,3-hexafluoroacetone with stirring using a stirrer at a temperature range of 50 to 60° C. by spending 2 hr. Upon this, the pressure was 0.5 MPa. After introducing 1,1,1,3,3,3-hexafluoroacetone, the reaction liquid was stirred at a temperature of 50 to 60° C. for 5 hr. When the pressure lowered to 0.1 MPa, the reaction was terminated. As a result, 35.0 g of a reaction mixture were obtained. The reaction liquid, except excessive acetophenone, was found by gas chromatography to contain 95.1% of the target 4,4,4-trifluoro-3-hydroxy-1-phenyl-3-(trifluoromethyl)butan-1-one and 4.9% of impurities. 35.0 g of the obtained reaction mixture were subjected to a vacuum distillation under 2.9 kPa, thereby collecting a distillate having a boiling point range of 135 to 137° C. With this, there were obtained 28.1 g of the target 4,4,4-trifluoro-3-hydroxy-1-phenyl-3-(trifluoromethyl)butan-1-one (purity: 98.0%). The yield was 80.2%.

The NMR data of the target product are as follows.

$^1$H NMR (solvent: CDCl$_3$; standard substance: TMS); δ 7.94–7.97 (m, 2H), 7.66–7.71 (m, 1H), 7.50–7.55 (m, 1H), 7.21 (s, 1H), 3.46 (s, 2H) $^{19}$F NMR (solvent: CDCl$_3$; standard substance: CCl$_3$F); δ −78.5 (s, 6F).

EXAMPLE 12

1st Step

Production of 1-[2,2,2-trifluoro-1-hydroxy-1-(trifluoromethyl)ethyl]-1,3-dihydro-2H-inden-2-one A 100 mL pressure-proof glass reactor equipped with a pressure gauge, a thermometer and a gas introducing tube was charged with a stirring magnet coated with tetrafluoroethylene resin, 20.0 g (0.15 moles) of 2-indanone, 0.04 g of concentrated sulfuric acid and 20.0 g of hexane, followed by introducing 24.0 g (0.15 moles) of 1,1,1,3,3,3-hexafluoroacetone with stirring using a stirrer at a temperature range of 30 to 55° C. by spending 2 hr. Upon this, the pressure was 0.5 MPa. After introducing 1,1,1,3,3,3-hexafluoroacetone, the reaction liquid was stirred at a temperature of 50 to 55° C. for 7 hr. When the pressure lowered to 0.1 MPa, the reaction was terminated. As a result, 35.0 g of a reaction mixture were obtained. The reaction liquid was found by gas chromatography to contain 94.6% of the target 1-[2,2,2-trifluoro-1-hydroxy-1-(trifluoromethyl)ethyl]-1,3-dihydro-2H-inden-2-one and 4.5% of 2-indanone. The hexane (solvent) was distilled out, and 34.3 g of the obtained reaction mixture were subjected to a vacuum distillation under 0.4 kPa, thereby collecting a distillate having a boiling point range of 100 to 102° C. With this, there were obtained 19.6 g of the target 1-[2,2,2-trifluoro-1-hydroxy-1-(trifluoromethyl)ethyl]-1,3-dihydro-2H-inden-2-one (purity: 95.2%) containing 4.3% of the raw material 2-indanone. The yield was 41.7%.

The NMR data of the target product are as follows.

$^1$H NMR (solvent: CDCl$_3$; standard substance: TMS); δ 7.30–7.53 (m, 4H), 6.36 (s, 1H), 3.99 (s, 1H), 3.73 (dd, J=68.55 Hz, 23.66 Hz, 2H) $^{19}$F NMR (solvent: CDCl$_3$; standard substance: CCl$_3$F); δ −74.68 (q, J=9.16 Hz, 3F), −73.34 (q, J=9.16 Hz, 3F)

EXAMPLE 13

2nd Step

Production of 1,1,1-trifluoro-2-(trifluoromethyl) pentane-2,4-diol

A 1 L pressure-proof stainless steel (SUS316) reactor equipped with a pressure gauge, a thermometer and a stirrer was charged with 150 ml of diisopropyl ether, 300 g (1.34 moles) of 1,1,1-trifluoro-2-hydroxy-2-(trifluoromethyl)pentan-4-one and 30.0 g of 5% Ru/C (i.e., a ruthenium catalyst wherein Ru is carried on activated carbon; water content: 50%; made by N.E. CHEMCAT CORPORATION located in Tokyo, Japan). The atmosphere of the reactor was replaced with hydrogen, and then the hydrogen pressure was adjusted to 0.6 MPa. The reactor was heated in an oil bath to have an internal temperature of 80° C. 9 hr later the temperature was lowered to room temperature, thereby terminating the reaction. The sampled reaction liquid, except diisopropyl ether used as a solvent, was found by gas chromatography to contain 100% 1,1,1-trifluoro-2-(trifluoromethyl)pentane-2,4-diol. The ruthenium catalyst was separated from the reaction liquid, thereby obtaining 293 g of a filtrate. This filtrate was subjected to a vacuum distillation under 0.65 kPa, thereby collecting a distillate having a boiling point range of 58 to 60° C. With this, there were obtained 270 g of the target 1,1,1-trifluoro-2-(trifluoromethyl)pentane-2,4-diol (purity: 99.0%). The yield was 88.2%.

The NMR data of the target product are as follows.
$^1$H NMR (solvent: CDCl$_3$; standard substance: TMS); δ 6.62 (s, 1H), 4.44 (m, 1H), 2.79 (d, J=3.90 Hz, 1H), 2.04 (m, 2H), 1.30 (d, J=6.10 Hz, 3H) $^{19}$F NMR (solvent: CDCl$_3$; standard substance: CCl$_3$F); δ −76.2 (q, J=10.7 Hz, 3F), −80.0 (q, J=10.7 Hz, 3F)

EXAMPLE 14

2nd Step

Production of 1,1,1-trifluoro-2-(trifluoromethyl)hexane-2,4-diol

A 1 L pressure-proof stainless steel (SUS316) reactor equipped with a pressure gauge, a thermometer and a stirrer was charged with 135 ml of diisopropyl ether, 140 g (0.59 moles) of a mixture containing 97.00% 6,6,6-trifluoro-5-hydroxy-5-(trifluoromethyl)hexan-3-one and 2.40% 5,5,5-trifluoro-4-hydroxy-3-methyl-4-(trifluoromethyl)pentan-2-one, and 14.0 g of 5% Ru/C which was the same as that of Example 13. The atmosphere of the reactor was replaced with hydrogen, and then the hydrogen pressure was adjusted to 0.6 MPa. The reactor was heated in an oil bath to have an internal temperature of 66° C. 8 hr later the temperature was lowered to room temperature, thereby terminating the reaction. The sampled reaction liquid, except diisopropyl ether used as a solvent, was found by gas chromatography to contain 97.0% 1,1,1-trifluoro-2-(trifluoromethyl)hexane-2,4-diol and 2.40% 1,1,1-trifluoro-3-methyl-2-(trifluoromethyl)pentane-2,4-diol. The ruthenium catalyst (5% Ru/C) was separated from the reaction liquid. The resulting filtrate was subjected to a vacuum concentration, thereby obtaining 137 g of a mixture containing 95.20% of the target 1,1,1-trifluoro-2-(trifluoromethyl)hexane-2,4-diol, 2.30% of 1,1,1-trifluoro-3-methyl-2-(trifluoromethyl)pentane-2,4-diol, and 1.90% of diisopropyl ether. This mixture was subjected to a vacuum distillation under 2.0 kPa, thereby collecting a distillate having a boiling point range of 87.0 to 87.5° C. With this, there were obtained 120 g of a product mixture containing 99.10% of the target 1,1,1-trifluoro-2-(trifluoromethyl)hexane-2,4-diol and 0.90% of 1,1,1-trifluoro-3-methyl-2-(trifluoromethyl)pentane-2,4-diol. The yield of 1,1,1-trifluoro-2-(trifluoromethyl)hexane-2,4-diol was 86.5%.

The NMR data of the target product are as follows.
$^1$H NMR (solvent: CDCl$_3$; standard substance: TMS); δ 6.53 (s, 1H), 4.17 (m, 1H), 2.64 (bs, 1H), 2.03 (m, 2H), 1.57 (m, 2H), 0.97 (t, J=7.56 Hz, 3H) $^{19}$F NMR (solvent: CDCl$_3$; standard substance: CCl$_3$F); δ −76.1 (q, J=9.16 Hz, 3F), −80.0 (q, J=10.68 Hz, 3F)

EXAMPLE 15

2nd Step

Production of 2-[2,2,2-trifluoro-1-hydroxy-1-(trifluoromethyl)ethyl]cyclopentanol A 100 ml pressure-proof glass reactor equipped with a thermometer and a pressure gauge was charged with a stirring magnet coated with tetrafluoroethylene resin, 5.0 g (20.0 mmol) of 2-[2,2,2-trifluoro-1-hydroxy-1-(trifluoromethyl)ethyl]cyclopentanone, 0.5 g of 5% Ru/C which was the same as that of Example 13, and 20 mL of diisopropyl ether. The atmosphere of the reactor was replaced with hydrogen, and then the hydrogen pressure was adjusted to 0.6 MPa. The reactor was heated in an oil bath with stirring using a stirrer to have an internal temperature of 85° C. 4 hr later the temperature was lowered to room temperature, thereby terminating the reaction. The sampled reaction liquid, except diisopropyl ether used as a solvent, was found by gas chromatography to contain 97.2% of the target 2-[2,2,2-trifluoro-1-hydroxy-1-(trifluoromethyl)ethyl]cyclopentanol, 0.1% of the raw material 2-[2,2,2-trifluoro-1-hydroxy-1-(trifluoromethyl)ethyl]cyclopentanone, and 2.7% of impurities. The ruthenium catalyst (5% Ru/C) was separated from the reaction liquid. The resulting filtrate was subjected to a vacuum distillation under 2.93 kPa, thereby collecting a distillate having a boiling point range of 113 to 115° C. With this, there were obtained 4.18 g of the target. 2-[2,2,2-trifluoro-1-hydroxy-1-(trifluoromethyl)ethyl]cyclopentanol (purity: 99.3%). The yield was 82.3%.

The NMR data of the target product are as follows.
$^1$H NMR (solvent: CDCl$_3$; standard substance: TMS); δ 6.32 (s, 1H), 4.72–4.74 (m, 1H), 2.33 (d, J=2.93 Hz, 1H), 1.68–2.23 (m, 7H) $^{19}$F NMR (solvent: CDCl$_3$; standard substance: CCl$_3$F); δ −75.05 (q, J=12.21 Hz, 3F), −75.78 (q, J=12.21 Hz, 3F)

EXAMPLE 16

2nd Step

Production of 1-[2,2,2-trifluoro-1-hydroxy-1-(trifluoromethyl)ethyl]indan-2-ol A 100 ml pressure-proof glass reactor equipped with a thermometer and a pressure gauge was charged with a stirring magnet coated with tetrafluoroethylene resin, 15.0 g (50.3 mmol) of 1-[2,2,2-trifluoro-1-hydroxy-1-(trifluoromethyl)ethyl]-1,3-dihydro-2H-inden-2-one, 1.5 g of 5% Ru/C which was the same as that of Example 13, and 10.5 g of diisopropyl ether. The atmosphere of the reactor was replaced with hydrogen, and then the hydrogen pressure was adjusted to 0.6 MPa. The reactor was heated in an oil bath with stirring using a stirrer to have an internal temperature of 70° C. 48 hr later the temperature was lowered to room temperature, thereby terminating the reaction. The sampled reaction liquid, except diisopropyl ether used as a solvent, was found by gas chromatography to contain 96.5% of the target 1-[2,2,2-trifluoro-1-hydroxy-1-(trifluoromethyl) ethyl]indan-2-ol, 2.3% of the raw material 2-indanone, and 1.2% of impurities. The ruthenium catalyst (5% Ru/C) was separated from the reaction liquid. The resulting filtrate was subjected to a vacuum distillation under 0.4 kPa, thereby collecting a distillate having a boiling point range of 120 to 126° C. With this, there were obtained 12.7 g of the target 1-[2,2,2-trifluoro-1-hydroxy-1-(trifluoromethyl)ethyl]indan-2-ol (purity: 97.7%). The yield was 82.2%.

The NMR data of the target product are as follows.

$^1$H NMR (solvent: CDCl$_3$; standard substance: TMS); δ 7.15–7.40 (m, 4H), 6.62 (bs, 1H), 5.06 (q, J=7.56 Hz, 1H), 3.96 (d, J=7.32 Hz, 1H), 3.19 (qd, J=15.25 Hz, 8.05 Hz, 2H), 2.84 (bs, 1H) $^{19}$F NMR (solvent: CDCl$_3$; standard substance: CCl$_3$F); δ −74.59 (d, J=7.63 Hz, 3F), −72.06 (d, J=9.16 Hz, 3F)

EXAMPLE 17

3rd Step

Production of 4,4,4-trifluoro-3-hydroxy-1-methyl-3-(trifluoromethyl)butyl 2-methylacrylate A 1000 ml four-necked flask equipped with a thermometer and a reflux condenser was charged with a stirring magnet coated with tetrafluoroethylene resin, 100.0 g (0.44 mol) of 1,1-bis(trifluoromethyl)butane-1,3-diol, 300 g of toluene, 58.7 g (0.48 mol) of 2,6-dimethylpyridine, 68.99 g (0.66 mol) of methacrylic chloride, and 0.5 g of NONFLEX MBP, followed by heating in an oil bath with stirring using a stirrer to have an internal temperature of 95–100° C. 6 hr later the composition was found by gas chromatography to contain 89.0% of the target 4,4,4-trifluoro-3-hydroxy-1-methyl-3-(trifluoromethyl)butyl 2-methylacrylate, 1.9% of the raw material 1,1-bis(trifluoromethyl)butane-1,3-diol, and 9.1% of others.

After cooling the reaction liquid, the by-product 2,6-dimethylpyridine hydrochloride was removed by filtration. The resulting filtrate was washed with 100 g of 10% hydrochloric acid aqueous solution. The resulting aqueous layer was extracted with 150 g of diisopropyl ether. The thus obtained two organic layers were combined together, followed by washing with 150 g of 10% brine two times. The resulting organic layer was dried with 30 g of magnesium sulfate, followed by removing magnesium sulfate by filtration. To the resulting filtrate 0.7 g of phenothiazine (a polymerization inhibitor) were added, followed by distilling the solvent out. Then, the reaction liquid was subjected to a vacuum distillation under 10 Torr (1.33 kPa), thereby collecting a distillate having a boiling point range of 85 to 88° C. With this, there were obtained 75.0 g of 4,4,4-trifluoro-3-hydroxy-1-methyl-3-(trifluoromethyl)butyl 2-methylacrylate. This distillate was found by gas chromatography to contain 98.52% of the target 4,4,4-trifluoro-3-hydroxy-1-methyl-3-(trifluoromethyl)butyl 2-methylacrylate, 0.35% of the raw material 1,1-bis(trifluoromethyl)butane-1,3-diol, and 1.13% of others. The yield was 57.1%.

The NMR data of the target product are as follows.

$^1$H NMR (solvent: CDCl$_3$; standard substance: TMS); δ 6.16 (q, J=0.98 Hz, 1H), 5.96 (bs, 1H), 5.66 (q, J=1.46 Hz, 1H), 5.13–5.20 (m, 1H), 2.24–2.36 (m, 2H), 1.94 (dd, J=1.46 Hz, 0.98 Hz, 3H), 1.44 (d, J=6.34 Hz, 3H) $^{19}$F NMR (solvent: CDCl$_3$; standard substance: CCl$_3$F); δ −77.03 (q, J=9.67 Hz, 3F), −79.25 (q, J=9.67 Hz, 3F)

EXAMPLE 18

3rd Step

Production of 4,4,4-trifluoro-3-hydroxy-1-methyl-3-(trifluoromethyl)butyl 2-methylacrylate A 1000 ml three-necked flask equipped with a thermometer and a reflux condenser was charged with a stirring magnet coated with tetrafluoroethylene resin, 100.0 g (0.44 moles) of 1,1-bis(trifluoromethyl)butane-1,3-diol, 74.6 g (0.48 mol) of methacrylic acid anhydride, 4.23 g (0.044 mol) of methanesulfonic acid, 400 g of toluene, and 0.5 g of phenothiazine, followed by heating at 50° C. in an oil bath under reflux with stirring using a stirrer. 4 hr later the reaction liquid was analyzed by gas chromatography. With this, the reaction liquid, except the by-product methacrylic acid, was found to contain 94.5% of the target 4,4,4-trifluoro-3-hydroxy-1-methyl-3-(trifluoromethyl)butyl 2-methylacrylate, 1.6% of the raw material 1,1-bis(trifluoromethyl)butane-1,3-diol, 2.0% of methacrylic acid anhydride, and 1.9% of others.

After washing the reaction liquid with 200 g of water two times, the obtained organic layer was dried with 30 g of magnesium sulfate, followed by removing magnesium sulfate by filtration. To the resulting filtrate 0.7 g of phenothiazine were added, followed by distilling the solvent out. Then, the reaction liquid was subjected to a vacuum distillation under 8 Torr (1.07 kPa), thereby collecting a distillate having a boiling point range of 80 to 82° C. With this, there were obtained 77.5 g of 4,4,4-trifluoro-3-hydroxy-1-methyl-3-(trifluoromethyl)butyl 2-methylacrylate. This distillate was found by gas chromatography to contain 98.2% of the target 4,4,4-trifluoro-3-hydroxy-1-methyl-3-(trifluoromethyl)butyl 2-methylacrylate, 0.2% of the raw material 1,1-bis(trifluoromethyl)butane-1,3-diol, and 1.6% of others. The yield was 58.8%.

The NMR data of the target product were the same as those of Example 17.

COMPARATIVE EXAMPLE 1

Production of 1,1,1-trifluoro-2-(trifluoromethyl)pentan-4-one

A 1 L pressure-proof stainless steel (SUS316) reactor equipped with a pressure gauge, a thermometer and a stirrer was charged with 261.35 g (4.50 moles) of acetone and 498.0 g (3.00 moles) of 1,1,1,3,3,3-hexafluoroacetone, followed by heating in an oil bath to have an internal temperature of 100° C. Upon this, the pressure was 1.70 MPa. The reaction was conducted for 41 hr while the internal temperature was controlled within a range of 100 to 120° C. to adjust the pressure to 2.0 MPa or lower. With this, however, the pressure lowering was not found. The reaction liquid was cooled down to room temperature to terminate the reaction, thereby obtaining 336.5 g of a reaction mixture. The sampled reaction liquid was found by gas chromatography to contain 72.20% of acetone, 21.36% of the target 1,1,1-trifluoro-2-(trifluoromethyl)pentan-4-one, 5.75% of 1,3-bis (2'-hydroxy-1',1',1',3',3',3'-hexapropyl)acetone as an impurity, and 0.69% of other impurities. The obtained reaction mixture was subjected to a vacuum distillation under 4.8 kPa, thereby collecting a distillate having a boiling point range of 67 to 68° C. With this, there were obtained 79.3 g of the target 1,1,1-trifluoro-2-(trifluoromethyl)pentan-4-one (purity: 99.5%). The yield was 11.7%.

It was found by Comparative Example 1 that, in the case of reacting hexafluoroacetone with acetone under a pressure lower than 2 MPa without using catalyst, the reaction temperature becomes around 100° C., and the reaction proceeds by a degree of only ⅕ of that of the case of adding the additive, even if the reaction is conducted for 40 hr or longer.

COMPARATIVE EXAMPLE 2

A 100 mL pressure-proof glass reactor equipped with a pressure gauge, a thermometer and a stirrer was charged with 15 ml of tetrahydrofuran, 10 g (0.0446 mol) of 1,1,1-trifluoro-2-hydroxy-2-(trifluoromethyl)pentan-4-one, and 1.0 g of 10% Pd/C (i.e., a palladium catalyst wherein Pd is carried on activated carbon; water content: 50%; made by N.E. CHEMCAT CORPORATION). The atmosphere of the reactor was replaced with hydrogen, and then the hydrogen pressure was adjusted to 0.6 MPa. The reactor was heated in an oil bath to have an internal temperature of 100° C. 9 hr later the temperature was lowered to room temperature. The sampled reaction liquid, except tetrahydrofuran used as the solvent, was found by gas chromatography to contain 100% of the raw material 1,1,1-trifluoro-2-hydroxy-2-(trifluoromethyl)pentan-4-one. In other words, the reaction did not proceed at all in Comparative Example 2, in which Pd/C was used as the catalyst.

COMPARATIVE EXAMPLE 3

A 100 mL pressure-proof glass reactor equipped with a pressure gauge, a thermometer and a stirrer was charged with 15 ml of tetrahydrofuran, 10 g (0.0446 mol) of 1,1,1-trifluoro-2-hydroxy-2-(trifluoromethyl)pentan-4-one, and 1.0 g of 2% Pt/C (a platinum catalyst wherein Pt is carried on activated carbon; water content: 50%; made by N.E. CHEMCAT CORPORATION). The atmosphere of the reactor was replaced with hydrogen, and then the hydrogen pressure was adjusted to 0.6 MPa. The reactor was heated in an oil bath to have an internal temperature of 100° C. 9 hr later the temperature was lowered to room temperature. The sampled reaction liquid, except tetrahydrofuran used as the solvent, was found by gas chromatography to contain 3.0% of the target 1,1,1-trifluoro-2-(trifluoromethyl)pentan-2,4-diol and 97% of the raw material 1,1,1-trifluoro-2-hydroxy-2-(trifluoromethyl)pentan-4-one. In other words, the reduction into the target 1,1,1-trifluoro-2-(trifluoromethyl)pentan-2,4-diol proceeded only by 3.0% in Comparative Example 3, in which Pt/C was used as the catalyst.

What is claimed is:

1. A process for producing a fluorine-containing 2,4-diol represented by the formula [4],

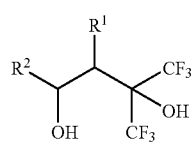

[4]

wherein $R^1$ represents a hydrogen atom or an acyclic or cyclic alkyl group having a carbon atom number of 1 to 7, $R^2$ represents an acyclic or cyclic alkyl group having a carbon atom number of 1 to 7, and $R^1$ and $R^2$ are optionally bonded to each other to form a ring, the process comprising reducing a hydroxy ketone represented by the formula [3],

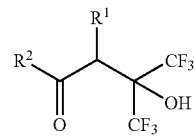

[3]

wherein $R^1$ and $R^2$ are defined as above, by hydrogen in the presence of a ruthenium catalyst.

2. A process according to claim 1, wherein the hydroxy ketone represented by the formula [3] is prepared by a process comprising reacting hexafluoroacetone represented by the formula [1],

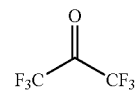

[1]

with a carbonyl compound represented by the formula [2],

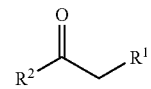

[2]

wherein $R^1$ and $R^2$ are defined as in the formula [4], in the presence of at least one compound selected from the group consisting of fluorine-containing alcohols, carboxylic acids, methanesulfonic acid, paratoluenesulfonic acid, fluorine-containing sulfonic acids, metal chlorides, inorganic acids, and $BF_3$.

3. A process according to claim 1, wherein the hydroxy ketone represented by the formula [3] is prepared by a process comprising reacting hexafluoroacetone represented by the formula [1],

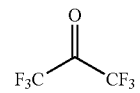

[1]

with a carbonyl compound represented by the formula [2],

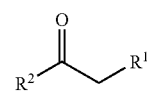

[2]

wherein R¹ and R² are defined as in the formula [4], in the presence of at least one compound selected from the group consisting of 1,1,1,3,3,3-hexafluoro-2-propanol, acetic acid, propionic acid, trifluoroacetic acid, methanesulfonic acid, paratoluenesulfonic acid, trifluoromethanesulfonic acid, aluminum chloride, tin chloride, iron chloride, titanium chloride, sulfuric acid, and BF₃.

4. A process according to claim 2, wherein the carbonyl compound represented by the formula [2] is one selected from the group consisting of acetone, methyl ethyl ketone, cyclopentanone, and cyclohexanone.

5. A process according to claim 4, wherein the carbonyl compound represented by the formula [2] is acetone.

6. A process according to claim 2, wherein the reacting is conducted at a temperature of 40 to 70° C. in the presence of at least one compound selected from the group consisting of carboxylic acids, methanesulfonic acid, paratoluenesulfonic acid, fluorine-containing sulfonic acids, metal chlorides, inorganic acids, and BF₃.

7. A process according to claim 2, wherein the reacting is conducted at a temperature of 80 to 110° C. in the presence of a fluorine-containing alcohol.

8. A process according to claim 1, wherein the ruthenium catalyst is one selected from the group consisting of metallic ruthenium, ruthenium carried on a carrier, a ruthenium salt, a ruthenium complex, and ruthenium oxide.

9. A process according to claim 8, wherein the ruthenium salt is selected from the group consisting of RuCl₃, RuBr₃, and Ru(NO₃)₃, and the ruthenium complex is selected from the group consisting of Ru(CO)₅, Ru(NO)₅, K₄[Ru(CN)₆], and Ru(phen)₃Cl₃ where phen represents a phenanthroline.

10. A process according to claim 8, wherein the ruthenium catalyst is a solid-phase catalyst in which ruthenium is carried on an activated carbon, alumina, or silica.

11. A process according to claim 1, wherein, prior to the reducing, atmosphere of a reactor for conducting the reducing is replaced with hydrogen gas.

12. A process according to claim 1, wherein the reducing is conducted in a solvent that is at least one selected from the group consisting of aromatic compounds, ethers, and alcohols.

13. A process according to claim 12, wherein the aromatic compounds are benzene, toluene, xylene and mesitylene, the ethers are diethyl ether, methyl-tert-butyl ether, diisopropyl ether and tetrahydrofuran, and alcohols are methanol, ethanol, propanol, 2-propanol, trifluoroethanol and 1,1,1,3,3,3-hexafluoro-2-propanol.

14. A process according to claim 1, wherein the hydroxy ketone represented by the formula [3] is 1,1,1-trifluoro-2-hydroxy-2-(trifluoromethyl)pentane-2-one represented by the formula [3a],

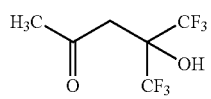

[3a]

wherein the fluorine-containing 2,4-diol represented by the formula [4] is 1,1,1-trifluoro-2-(trifluoromethyl)pentane-2,4-diol represented by the formula [4a]

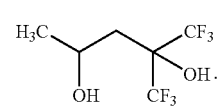

[4a]

15. A process according to claim 1, wherein the reducing is conducted at a temperature of 30 to 120° C. under a hydrogen pressure of 0.15 to 2 MPa in the presence of the ruthenium catalyst that is in an amount of 0.0002 to 0.04 moles, in terms of Ru atoms of the ruthenium catalyst, per mol of the hydroxy ketone.

16. A process for producing 1,1,1-trifluoro-2-(trifluoromethyl)pentane-2,4-diol represented by the formula [4a],

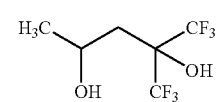

[4a]

the process comprising reducing 1,1,1-trifluoro-2-hydroxy-2-(trifluoromethyl)pentane-2-one represented by the formula [3a],

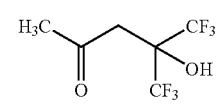

[3a]

by hydrogen, in the presence of a ruthenium catalyst, in which ruthenium is carried on an activated carbon, at a temperature of 30 to 120° C. under a hydrogen pressure of 0.15 to 2 MPa, wherein the ruthenium catalyst is in an amount of 0.0002 to 0.04 moles, in terms of Ru atoms of the ruthenium catalyst, per mol of the 1,1,1-trifluoro-2-hydroxy-2-(trifluoromethyl)pentane-2-one represented by the formula [3a].

17. A process according to claim 16, wherein the 1,1,1-trifluoro-2-hydroxy-2-(trifluoromethyl)pentane-2-one represented by the formula [3a] is prepared by a process comprising reacting hexafluoroacetone with acetone in the presence of sulfuric acid at a temperature of 40 to 70° C.

18. A process for producing a fluorine-containing ester compound represented by the formula [6],

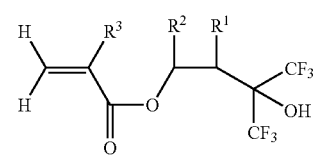

[6]

wherein R¹ represents a hydrogen atom or an acyclic or cyclic alkyl group having a carbon atom number of 1 to 7, R² represents an acyclic or cyclic alkyl group having a carbon atom number of 1 to 7, and $R^1$ and $R^2$ are optionally bonded to each other to form a ring, and $R^3$ represents H, $C_mH_{m+1}$, or $C_nF_{2n+1}$ where each of m and n represents independently an integer of 1 to 4, the process comprising the steps of:

(a) reducing a hydroxy ketone represented by the formula [3],

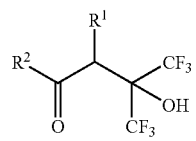

[3]

wherein $R^1$ and $R^2$ are defined as above, by hydrogen in the presence of a ruthenium catalyst, thereby producing a fluorine-containing 2,4-diol represented by the formula [4],

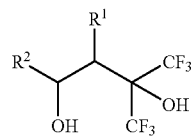

[4]

wherein $R^1$ and $R^2$ are defined as above, and (b) reacting the fluorine-containing 2,4-diol with an acrylic acid derivative represented by the formula [5],

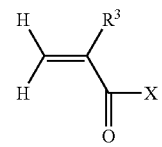

[5]

wherein $R^3$ is defined as in the formula [6], and X represents F, Cl, or a group represented by the formula [5a],

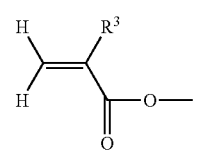

[5a]

wherein $R^3$ is defined as in the formula [6].

19. A process according to claim 18, wherein $R^3$ of the formula [6] represents H, methyl group or trifluoromethyl group.

20. A process according to claim 18, wherein, when X of the formula [5] represents F or Cl, the step (b) is conducted in the presence of a base.

* * * * *